(12) United States Patent
Luo et al.

(10) Patent No.: US 9,118,850 B2
(45) Date of Patent: Aug. 25, 2015

(54) CAMERA SYSTEM WITH MULTIPLE PIXEL ARRAYS ON A CHIP

(75) Inventors: Jiafu Luo, Irvine, CA (US); Kang-Huai Wang, Saratoga, CA (US); Gordon C. Wilson, San Francisco, CA (US)

(73) Assignee: Capso Vision, Inc., Saratoga, CA (US)

( * ) Notice: Subject to any disclaimer, the term of this patent is extended or adjusted under 35 U.S.C. 154(b) by 1073 days.

(21) Appl. No.: 12/323,219

(22) Filed: Nov. 25, 2008

(65) Prior Publication Data

US 2009/0135245 A1    May 28, 2009

Related U.S. Application Data

(60) Provisional application No. 60/990,601, filed on Nov. 27, 2007.

(51) Int. Cl.
*H04N 7/00* (2011.01)
*H04N 5/341* (2011.01)
(Continued)

(52) U.S. Cl.
CPC .............. *H04N 5/3415* (2013.01); *A61B 1/041* (2013.01); *G02B 13/06* (2013.01); *H04N 5/23238* (2013.01); *H04N 5/378* (2013.01); *H04N 5/3745* (2013.01)

(58) Field of Classification Search
CPC ........................................ A61B 1/041
USPC ............................................. 348/36
See application file for complete search history.

(56) References Cited

U.S. PATENT DOCUMENTS 4,873,572 A    10/1989  Miyazaki et al.
5,510,623 A *  4/1996  Sayag et al. ............. 250/370.11
(Continued)

FOREIGN PATENT DOCUMENTS

JP    2001-304972      10/2001
WO      02054932 A2     7/2002
(Continued)

OTHER PUBLICATIONS

PCT International Search Report for International Application No. PCT/US2008/084852 dated Feb. 6, 2009, 3 pages.
(Continued)

*Primary Examiner* — Douglas Blair
(74) *Attorney, Agent, or Firm* — Edward C. Kwok; Hogan Lovells US LLP

(57) ABSTRACT

A camera system uses one or more image sensor IC chips each having multiple pixel arrays on the same semiconductor substrate (i.e., "multiple pixel arrays on a chip"). In one embodiment, such a camera system includes: (a) optical components that create multiple images in close physical proximity of each other (e.g., within a few millimeters or centimeters); and (b) a single sensor substrate ("chip") containing multiple 2-dimensional pixel arrays that are aligned to capture these multiple images, so as to convert the multiple images into electrical signal. The pixel arrays can be manufactured using a CCD or a CMOS compatible process. For manufacturing reasons, such a chip is typically two centimeters or less on a side. However, large chips can also be made. Optional electronic components for further signal processing of the captured images may be formed either on the sensor chip (i.e., in a "system-on-a-chip" implementation), or in a separate back-end application specific integrated circuit (ASIC). In addition, digital storage components, display elements, and wired or wireless communication links may also be included in any suitable combination to allow review and further processing of the captured images.

83 Claims, 8 Drawing Sheets

(51) Int. Cl.
- *A61B 1/04* (2006.01)
- *G02B 13/06* (2006.01)
- *H04N 5/232* (2006.01)
- *H04N 5/3745* (2011.01)
- *H04N 5/378* (2011.01)

(56) References Cited

U.S. PATENT DOCUMENTS

| | | | |
|---|---|---|---|
| 7,116,352 B2* | 10/2006 | Yaron | 348/45 |
| 7,144,366 B2* | 12/2006 | Takizawa et al. | 600/117 |
| 7,199,348 B2 | 4/2007 | Olsen et al. | |
| 7,423,784 B2* | 9/2008 | Tanabe et al. | 358/461 |
| 7,796,870 B2* | 9/2010 | Wang | 396/14 |
| 8,529,441 B2* | 9/2013 | Bandy et al. | 600/173 |
| 2002/0136550 A1* | 9/2002 | Kuwata et al. | 396/114 |
| 2003/0117491 A1* | 6/2003 | Avni et al. | 348/77 |
| 2004/0264630 A1 | 12/2004 | Bruder et al. | |
| 2005/0043586 A1* | 2/2005 | Suzushima | 600/160 |
| 2008/0030573 A1* | 2/2008 | Ritchey | 348/36 |
| 2008/0080028 A1* | 4/2008 | Bakin et al. | 358/514 |
| 2010/0261961 A1* | 10/2010 | Scott et al. | 600/111 |

FOREIGN PATENT DOCUMENTS

| | | |
|---|---|---|
| WO | 2007/051147 | 5/2007 |
| WO | 2007/126429 | 11/2007 |

OTHER PUBLICATIONS

PCT Written Opinion of the International Searching Authority for International Application No. PCT/US2008/084852 dated Feb. 6, 2009, 6 pages.

English Language Translation of JP Patent Application No. 2001-304972, published Oct. 31, 2001, pp. 1-8.

Office Action dated Jul. 10, 2012 in JP Patent Application No. 2010-536164, 3 pages.

English Language Translation of Office Action dated Jul. 10, 2012 in JP Patent Application No. 2010-536164, 3 pages.

Hansford, Wes "Multiproject Wafers Ease Analog/Mixed-Signal Design" Electronic Engineering Times, Feb. 5, 2007, p. 50.

Yoon, Kwangho et al. "Single-Chip CMOS Image Sensor for Mobile Applications" IEEE Journal of Solid-State Circuits, vol. 37, No. 12, Dec. 2002, pp. 1839-1845.

First European Examination Report for Application No. 08855600.6 dated Apr. 8, 2015, 5 pgs.

* cited by examiner

CAMERA SYSTEM WITH MULTIPLE PIXEL ARRAYS ON A CHIP

CROSS REFERENCE TO RELATED APPLICATIONS

The present application relates to and claims priority of U.S. Provisional Patent Application, entitled "Camera System with Multiple Arrays on a Chip," Ser. No. 60/990,601, filed Nov. 27, 2007. The disclosure of the Provisional Application is hereby incorporated by reference in its entirety.

BACKGROUND OF THE INVENTION

1. Field of the Invention

The present invention relates generally to optical camera systems. More specifically, the present invention relates to optical camera systems using integrated circuits (ICs) which integrate two or more separate imaging pixel arrays on a single IC chip.

2. Discussion of the Related Art

An optical camera system typically includes an optical lens or lens system, and light sensing elements. The light sensing elements can be either traditional film or integrated circuit sensors fabricated by any of a number of manufacturing processes, such as CMOS (complementary metal-oxide semiconductor) or CCD (charge-coupled device) process. Such light sensing ICs traditionally have light sensing elements, called pixels, arranged in a single one-dimensional (e.g., one row) or two-dimensional (e.g., many rows and columns) array. The pixel array is aligned with the image formed by the optical lens system and position within the focus depth of the optical system while each pixel provides an electrical output corresponding to the intensity of the incident light to which the pixel is exposed.

In a typical simple camera system, one image of an object is captured using a sensor chip having a pixel array. However, many applications require forming multiple images of the same object or forming multiple images of different objects. Such applications require using multiple cameras or, alternatively, a camera system with multiple sensor arrays. For example, a professional studio camcorder uses three sensor arrays to separately capture red, green, and blue images. As another example, a panoramic imaging system (e.g., that described in U.S. patent application Ser. No. 11/624,209) uses several sensor arrays to provide overlapping fields of view, so that a composite image may encompass a full 360° field of view.

For such applications, a conventional imaging system uses multiple single-array image sensor chips (e.g., CCD or CMOS sensors), with each sensor chip having a 2-dimensional pixel array located typically near the center of the sensor chip. In that arrangement, each sensor chip is fabricated separately and has its own signal processing chain, a digital image-processing pipeline or both. These chips are aligned and positioned carefully to accommodate the image-forming lens system. As a result, such a system has large power consumption due to duplicated signal chains on the chips. Such a system is also more complex and bulky due to difficulty in aligning multiple chips, and may be more costly to produce.

There is therefore a need for a simpler and more compact camera system that can take in multiple images.

SUMMARY OF THE INVENTION

The present invention provides a simpler and more compact camera system for capturing multiple images.

The present invention provides a camera system that uses one or more image sensor IC chips each having multiple pixel arrays on the same semiconductor substrate (i.e., "multiple pixel arrays on a chip"). In one embodiment, such a camera system includes: (a) optical components that create multiple images in close physical proximity of each other (e.g., within a few millimeters or centimeters); and (b) a single sensor substrate ("chip") containing multiple 2-dimensional pixel arrays that are aligned to capture these multiple images, so as to convert the multiple images into electrical signal. The pixel arrays can be manufactured using a CCD or a CMOS compatible process. For manufacturing reasons, such a chip is typically two centimeters or less on a side. However, large chips can also be made.

Optional electronic components for further signal processing of the captured images may be formed either on the sensor chip (i.e., in a "system-on-a-chip" implementation), or in a separate back-end application specific integrated circuit (ASIC). In addition, digital storage components, display elements, and wired or wireless communication links may also be included in any suitable combination to allow review and further processing of the captured images.

Compared to a conventional imaging system using multiple cameras or multiple image sensors, the present invention provides several advantages, such as a more compact design, easier fabrication, lower power, and a lower manufacturing cost. Other features and advantages of the present invention will become more readily apparent after reviewing the following detailed description and the accompanying drawings.

DETAILED DESCRIPTION OF THE PREFERRED EMBODIMENTS

Figure 1:
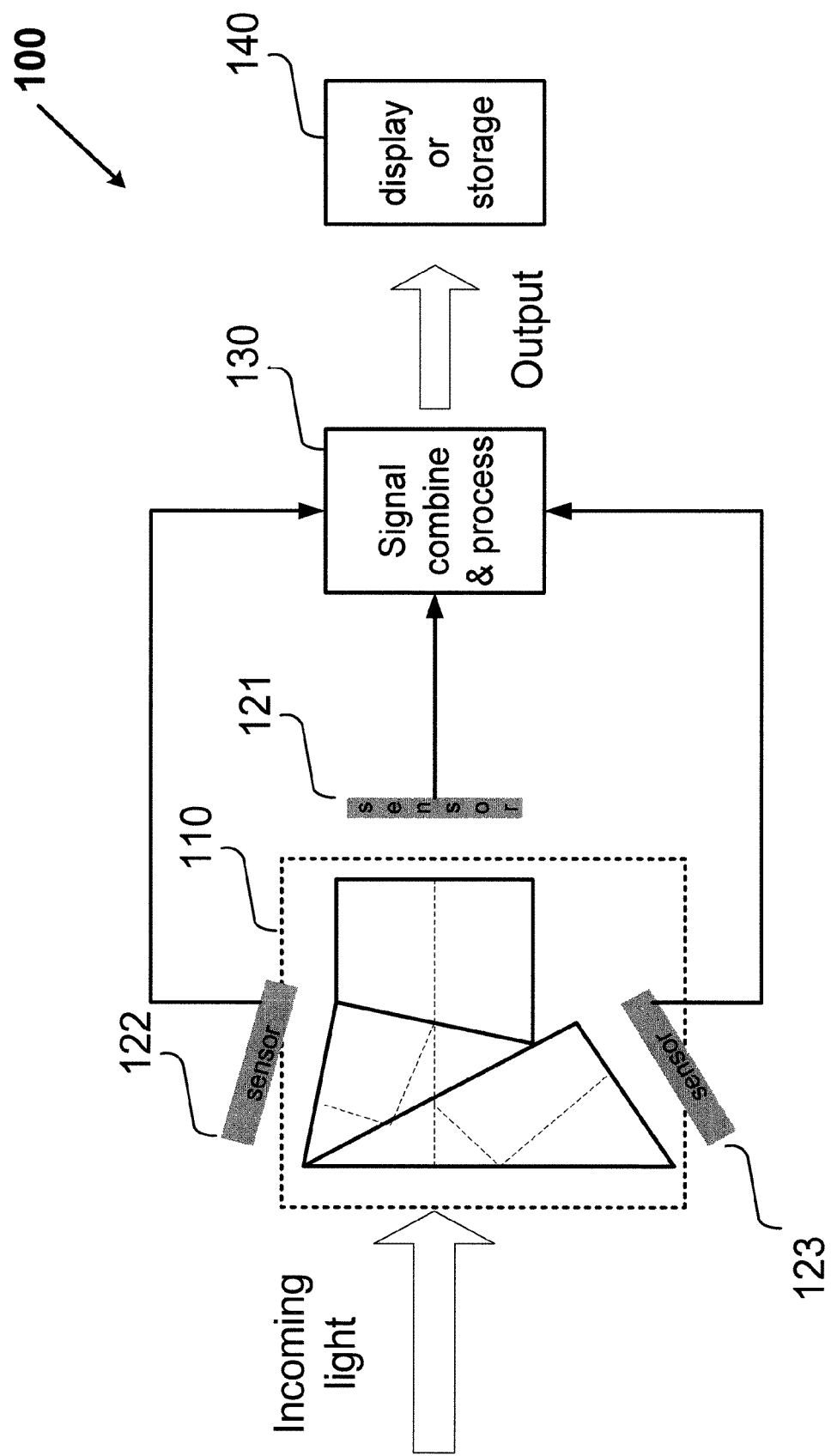
FIG. 1 shows a conventional camera system using multiple sensor chips.

The present invention provides a camera system having multiple pixel arrays on a semiconductor substrate ("on the chip"). FIG. 1 shows conventional camera system 100, having multiple image sensor chips. As shown in FIG. 1, camera system 100 includes optical system 110, multiple image sensor IC chips 121, 122, and 123, signal processing circuit 130, and display or storage element 140. Optical system 110, typically including lenses and beam splitters, forms multiple images from the incoming light. Multiple light sensing chips 121, 122, and 123 are aligned to the locations of these multiple images within the focus depth and convert the light sensed into electrical signals, in either analog or digital domain. Signal processing circuit 130 then combines the output signals from multiple image sensors 121, 122, and 123 for further processing. The output signals from signal processing circuit 130 are sent to display or storage element 140 for storage or display.

Figure 2:
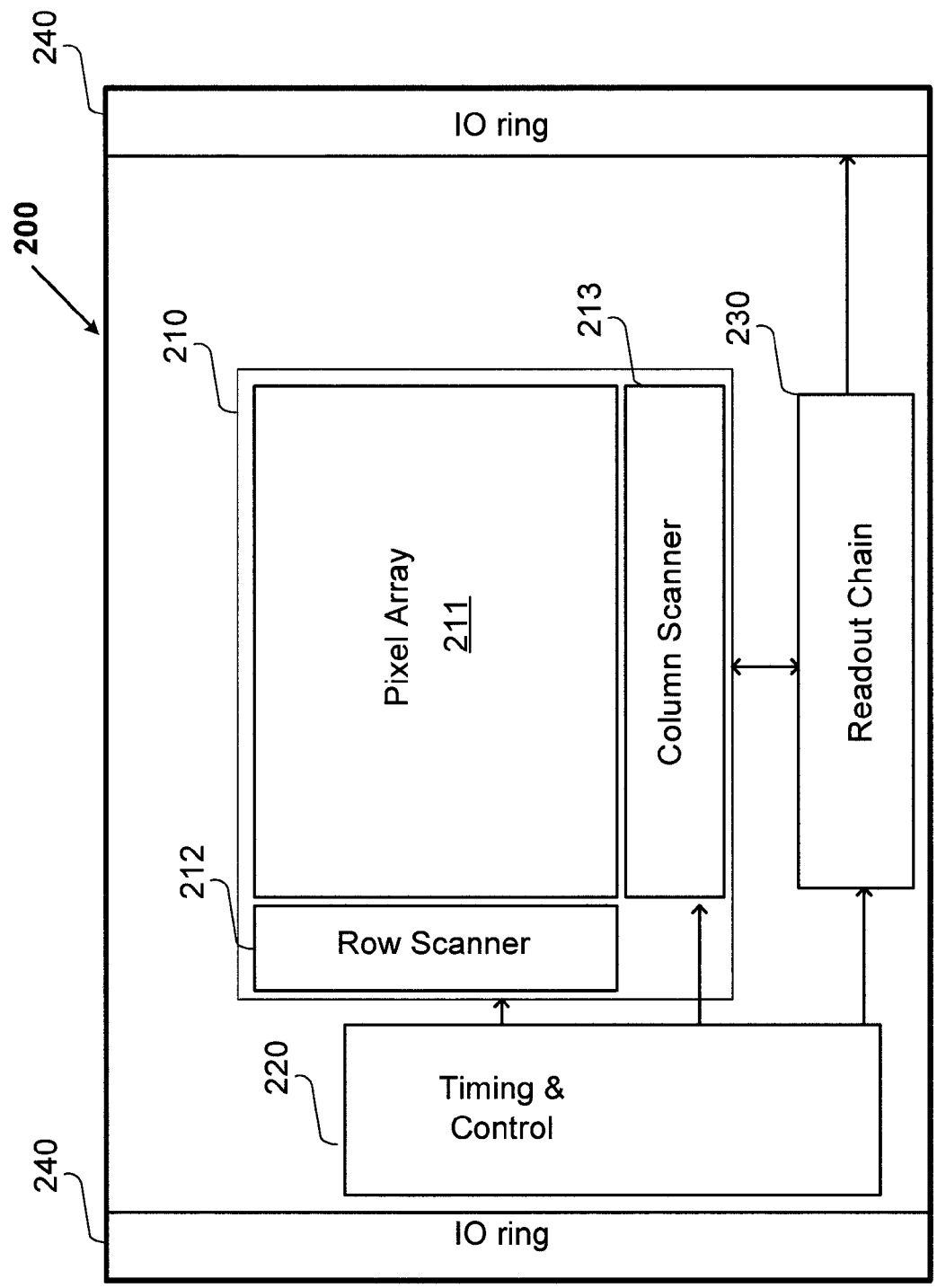
FIG. 2 shows a conventional integrated image sensor chip.

In camera system 100, multiple sensor chips 121, 122, and 123 can be the same kind or different kinds of integrated circuit chips. An example of such an image sensor chip is provided in FIG. 2 as sensor chip 200. The light sensing pixels in image sensor chip 200 are arranged into two-dimensional pixel array 211, provided substantially at the center. Row scanner 212 and column scanner 213 select the pixels to be reset or readout. Typically, pixel array 211, row scanner 212, and column scanner 213 are in close physical proximity of each other, usually referred to as block as sensor array 210. Besides sensor array 210, image sensor chip 200 may also include timing and control block 220, which generates some or all of the timing signals required for sensor chip operations. Readout chain block 230 may also be provided to process (in various degrees) the electrical output from the light-sensing pixels of block sensor array 210. Input and output signals of sensor chip 200 are handled by input/output (I/O) blocks 240.

In conventional camera system as system 100 of FIG. 1, aligning, positioning, and supporting multiple image sensor chips 121, 122, and 123 are required. For example, each image sensor chip must be aligned with its corresponding image plane. With each image sensor chip in its own package, such operations are not simple task and may substantially increase the manufacturing cost and the physical size of the camera system.

By a proper design, one can align the different image planes of optical system 110 to form a single plane. With such a design, multiple discrete image sensors may be placed on a common PC board to allow multiple images be recorded, with each image sensor recording a single image. In such a system, the size of the overall system is determined by how closely the active regions of the sensors may be packed together. A number of factors limit the packing density. First, the peripheral circuits (e.g., timing and control circuit 220, readout chain 230 and I/O ring 240) on each image sensing chip occupy space around each sensor array 210. The mechanical tolerances for wafer dicing and chip packaging must also be taken into account. Additionally, gaps are required on the PCB between sensor packages to allow reliably board assembly. Typically, each package has its own power, ground, and data pins. The closer the packages are placed relative to each other, the more difficult it is to route the interconnect signals on the PCB. Finally, each image sensor may require multiple power supply bypass capacitors, which must be placed close to the power pins. With so many constraints, size reduction in such a conventional camera system is difficult.

In principle, a sufficiently large conventional image sensor chip having a large pixel array can record images from multiple optical objectives onto a single light-sensing region. In such a case, the image sensor does not limit how closely the images can be packed together. Further, all the images in such a system share a common package, integrated power bus, signal processing circuitry and signal I/O pins. Therefore, the overall pin-count and the capacitor-count on the PCB are reduced. However, the mechanical and optical constraints still limit how closely the images can be packed on the sensor. As a result, many pixels cannot be used to form the resulting images. These unused pixels waste power and occupy precious chip real estate that may otherwise be used to provide other sensor functions.

Figure 3:
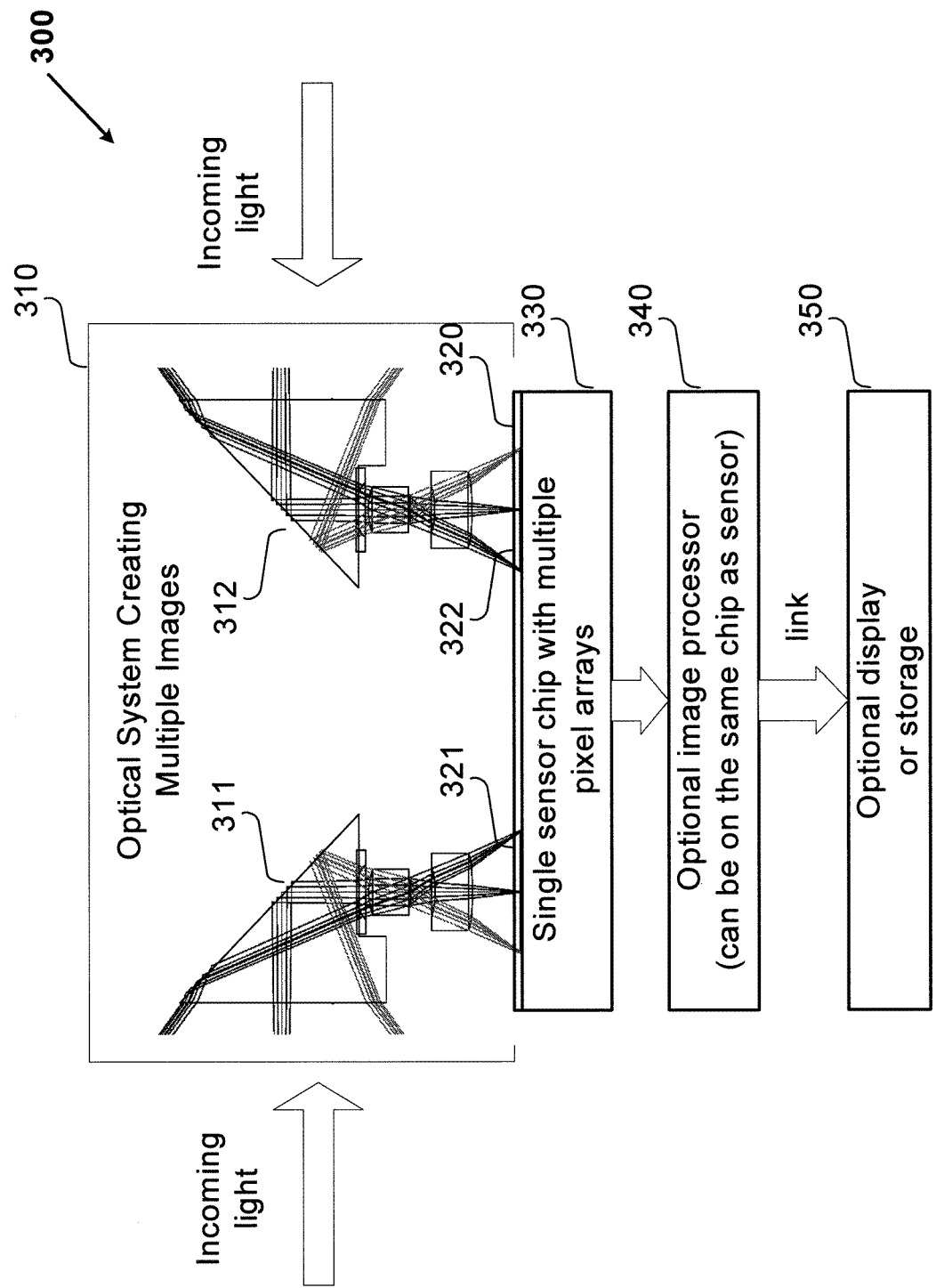
FIG. 3 shows an exemplary embodiment of the present invention, in which a camera system includes optical axes of two camera objectives that are oriented 180° apart in object space.

FIG. 3 shows camera system 300 having multiple pixel arrays on a chip, in accordance with one embodiment of the present invention. As shown in FIG. 3, camera system 300 includes (a) Optical system 310, which creates multiple images provided in close physical proximity of each other (e.g., within a few millimeters or centimeters), (b) single image sensor substrate ("chip") 330 providing multiple 2-dimensional pixel arrays at the locations of images formed by optical system 310 to capture the images; (c) optional electronic component 340, which further processes the captured images of sensor chip 330, and (d) optional component 350, which can be any combination of digital storage components, display elements, further processing elements, or transmission elements for wired or wireless communication.

Optical system 310 can have multiple elements for creating multiple images of the same object or of different objects. As shown in FIG. 3, optical system 310 includes lens sub-systems 311 and 312, with the optical axes of the objectives oriented 180° apart in object space, thereby forming images 321 and 322 on single image plane 320. More or less lens-systems can be included according to need. In practice, images 321 and 322 need not be aligned exactly onto a single image plane, but could have a small difference within the tolerance limit of optical system 310.

The pixel arrays of image chip 330 can be manufactured using either a CCD or a CMOS compatible process. For manufacturing reasons, such a chip is typically no more than two centimeters on a side. However, larger chips are also possible.

Optional electronic component 340 may be formed on sensor chip 330 (i.e., in a "system-on-a-chip" implementation), or on a separate back-end application specific integrated circuit (ASIC). Existing technology allows both analog and digital components to be formed on the same ASIC.

Optional component 350 allows review and further processing of the captured images.

Figure 4:
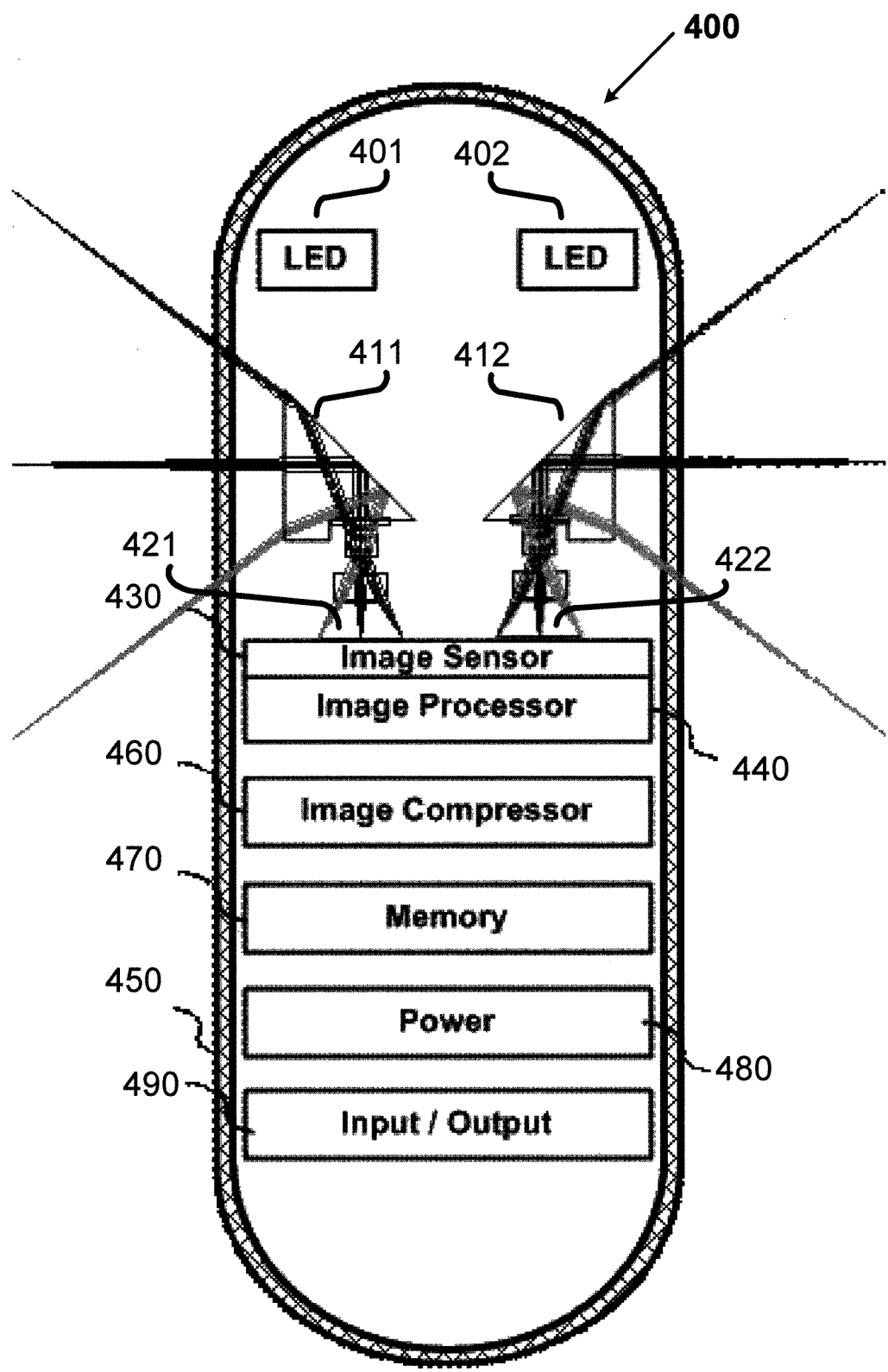
FIG. 4 shows camera system 400 provided inside a capsule housing, in accordance with one embodiment of the present invention.

FIG. 4 is a cross-section of camera system 400 in a swallowable capsule, in accordance with one embodiment of the present invention. Camera system 400 images human gastrointestinal (GI) tracts. Camera system 400 is substantially an implementation of camera system 300 inside capsule housing 450. In this embodiment, the optical system includes four lens sub-systems, although only lens sub-systems 411 and 412 are shown in FIG. 4. Two other lens sub-systems are provided in the orthogonal direction to the cross-section. Each lens sub-system forms a separate image (e.g., lens sub-systems 411 and 412 form images 421 and 422), which is captured in one of four multiple pixel arrays on image sensor chip 430. The output signals from all four pixel arrays are combined and digitized on image sensor chip 430 prior to further processing by image processor ASIC 440. Other components inside the capsule camera system 400 includes: (a) image compressor 450 for compressing the output images of image processor ASIC 440, so as to reduce the amount of data I/O; (b) memory block 470 for storing the compressed image; (c) power source 480, typically consisting of one or more batteries, for providing power to capsule camera system 400; (d) input/output block 490, which may include radio links, for communicating with an outside host; and (e) a lighting system, including multiple light-emitting diodes (LEDs) (e.g., LEDs 401, 402).

Figure 5:
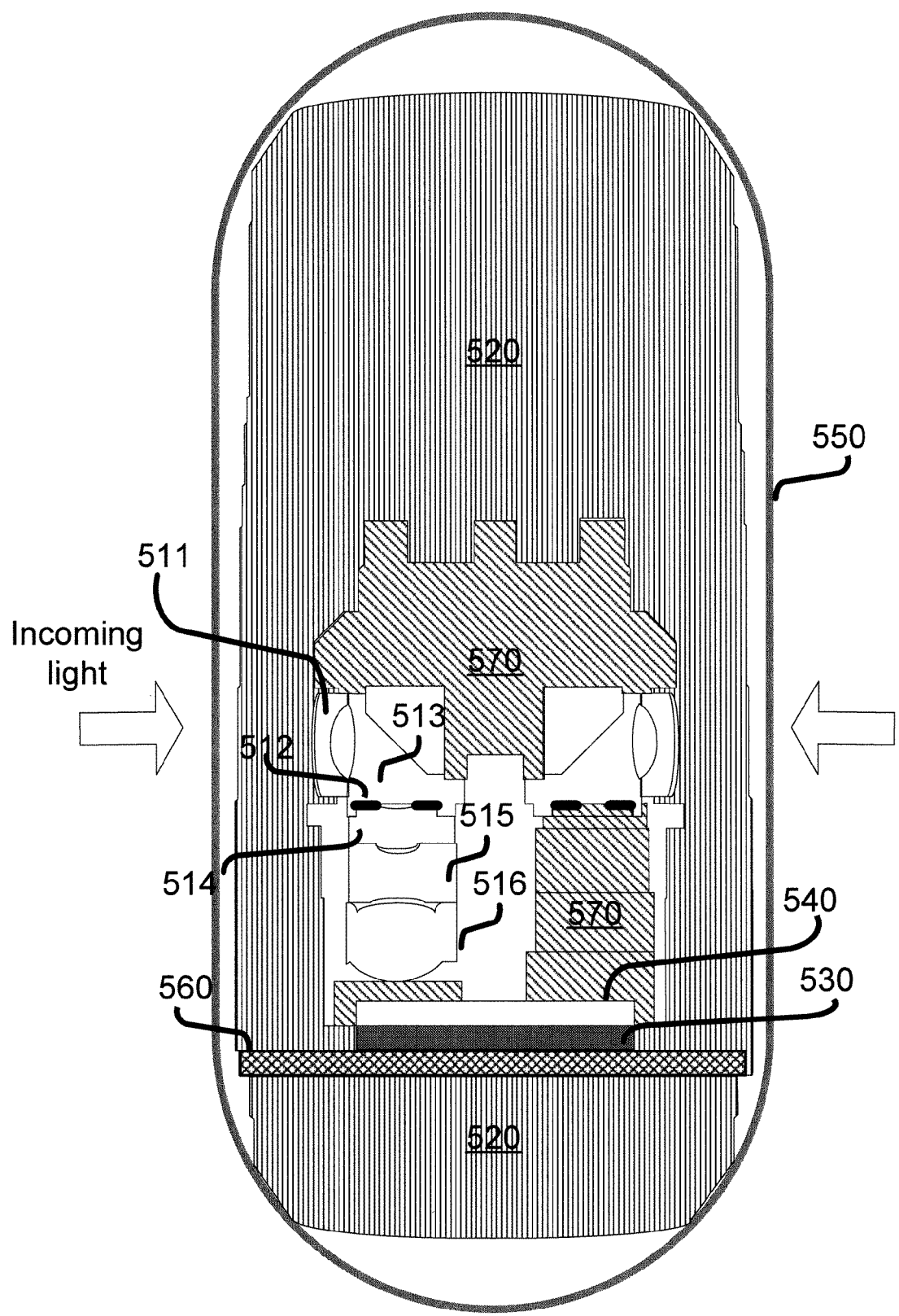
FIG. 5 shows in detail an optical system within a housing of a capsule camera, in accordance with one embodiment of the present invention.

FIG. 5 shows a cross-section through lens sub-systems 411 and 412 of the optical system of FIG. 4. The optical system of capsule camera system 400 is held together by a lens holder 520 within housing 550. The lens sub-systems, including lens subsystems 411 and 412, are enclosed by a lens barrel, which is a molded plastic part with a bore for each lens subsystem. As shown in FIG. 5, baffle 570 is provided on top of the lens barrel to block stray light between lens subsystems and to serve as a mechanical interface to parts above (not shown). Each lens sub-system includes of multiple lens elements (e.g., lens elements 511, 514, 515, and 516), aperture 512, and prism element 513. Image sensor 530 with multiple pixel arrays is provided to capture the images from the optical system. Image sensor 530 has a cover glass 540 that is provided during packaging, and is soldered onto printed circuit board (PCB) 560.

In this embodiment, lens element 511 has a negative power, while the lens group formed by lens elements 514, 515 and 516—a configuration often referred to as a "triplet"—has a positive power, together with suitable compensation for chromatic aberration. The overall lens configuration is a "folded inverse telephoto" lens design. Inverse telephoto is a common wide-angle lens configuration. Such a lens configuration for a capsule camera is disclosed, for example, in U.S. provisional patent application Ser. No. 61/052,180, entitled "Folded Imager," filed on May 10, 2008. The disclosure of the Imager Provisional Application is hereby incorporated by reference in its entirety.

As shown in FIG. 5, each lens sub-system has a horizontal field of view of at least 90°, with the optical axes of the lens sub-systems positioned 90° apart. By combining the four images from these four lens sub-systems, a panoramic image covering a 360° field of view can be reconstructed.

Figure 6:
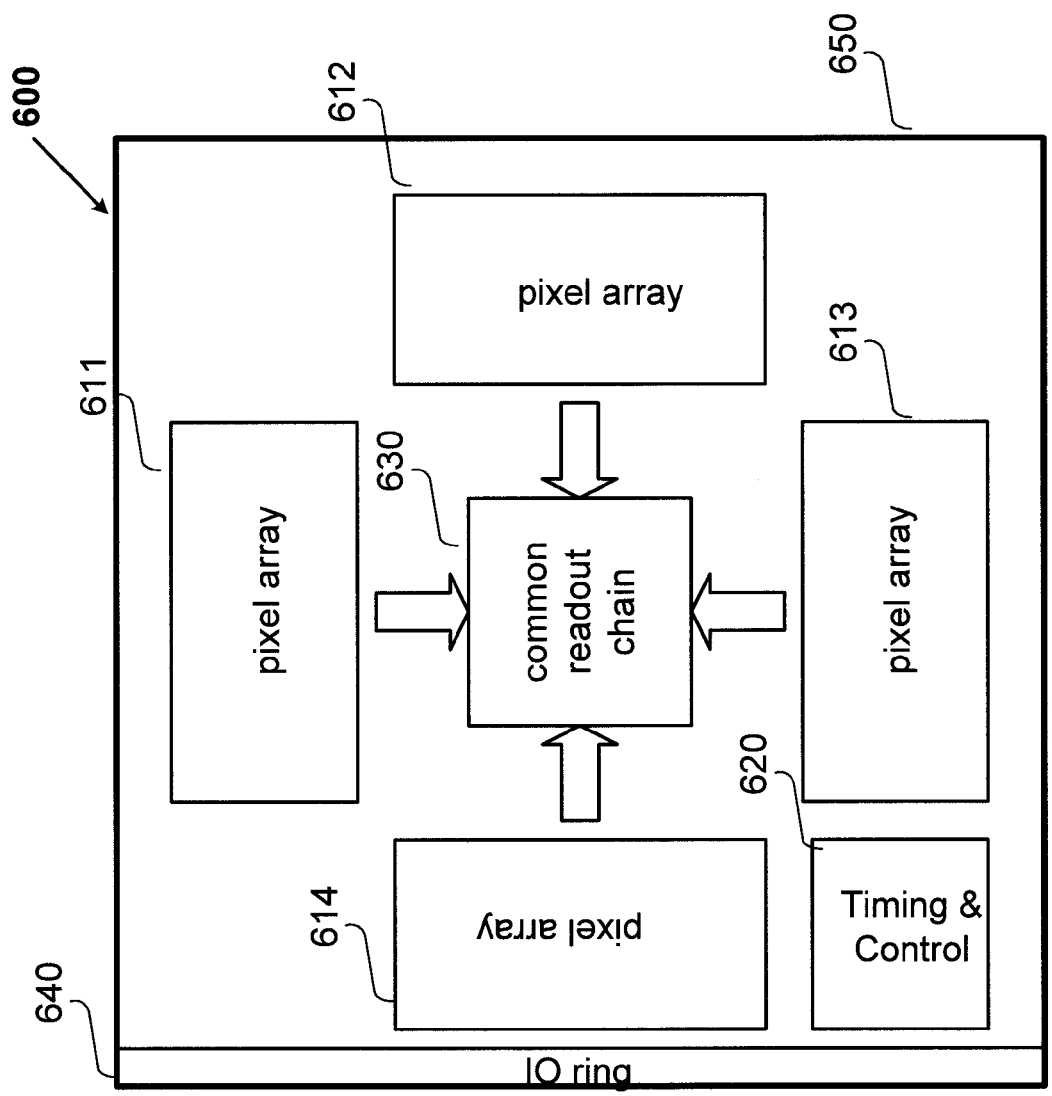
FIG. 6 shows an example of a single sensor chip having four 2-dimensional pixel arrays.

FIG. 6 shows an exemplary layout 600 for image sensor chip 430 of FIG. 4, in accordance with one embodiment of the invention. Layout 600 is provided on common substrate 650, typically a semiconductor material. On top of common substrate 650 are provided separate pixel arrays 611, 612, 613 and 614, provided at the expected locations of corresponding images formed by the four lens sub-systems. For example, pixel array 614 is provided to capture image 421 that is formed by lens sub-system 411, and pixel array 612 is provided to capture image 422 that is formed by lens sub-system 412. Each of these pixel arrays may be provided dedicated row and column scanners, or may share row and column scanners with other pixel arrays. The positions of the multiple pixel arrays are designed to accommodate the positions of the multiple images formed by the optical system. The distance between pixel arrays is typically on the order of millimeters, but may vary between tens of microns to several centimeters or inches.

Besides pixel arrays 611, 612, 613 and 614, other components may also be formed on substrate 650, including timing and control block 620, one or more readout chains (e.g., read out chain 630) for reading out electrical output signals from the pixel arrays, and I/O ring structures 640. Such components may have conventional constructions.

Figure 7:
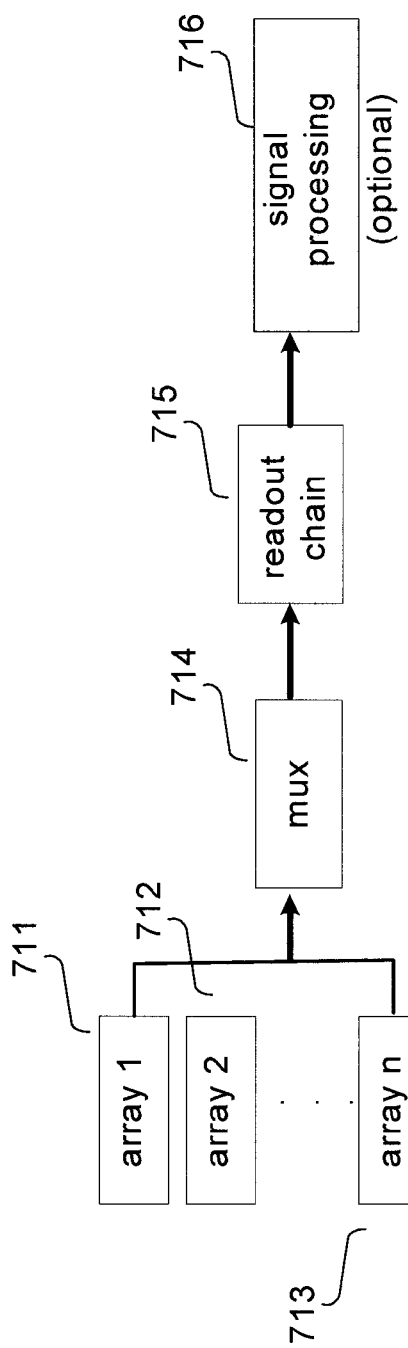
FIG. 7A shows multiple pixel arrays on a single sensor chip sharing a readout chain and an optional image-processing backend, according to a first approach to reading out and processing the output from the multiple pixel arrays.
FIG. 7B shows multiple pixel arrays each provided a separate readout chain, according to a second approach to reading out and processing the output from the multiple pixel arrays.
Figure 7:
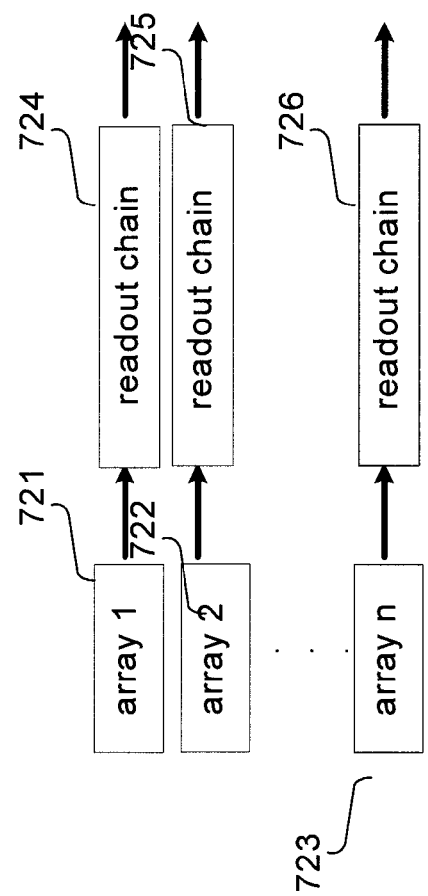

FIG. 7A and FIG. 7B show different approaches to reading out image data from the multiple pixel arrays. FIG. 7A, for example, shows pixel arrays 711, 712, . . . and 713 formed on a single sensor chip sharing readout chain 715 through multiplexer 714, according to a first approach. The data from readout chain 715 is provided to optional image-processing backend or processor 716. FIG. 7B shows pixel arrays 721, 722, . . . , and 723 being provided separate readout chains 724, 725, . . . , and 726, respectively, according to a second approach. Alternatively, a hybrid architecture combining the approaches of FIGS. 7A and 7B may be used. In such a hybrid architecture, output signals from some pixel arrays may be multiplexed for read out by a readout chain, while output signals from other pixel arrays may be multiplexed for read out by another readout chain.

Figure 8:
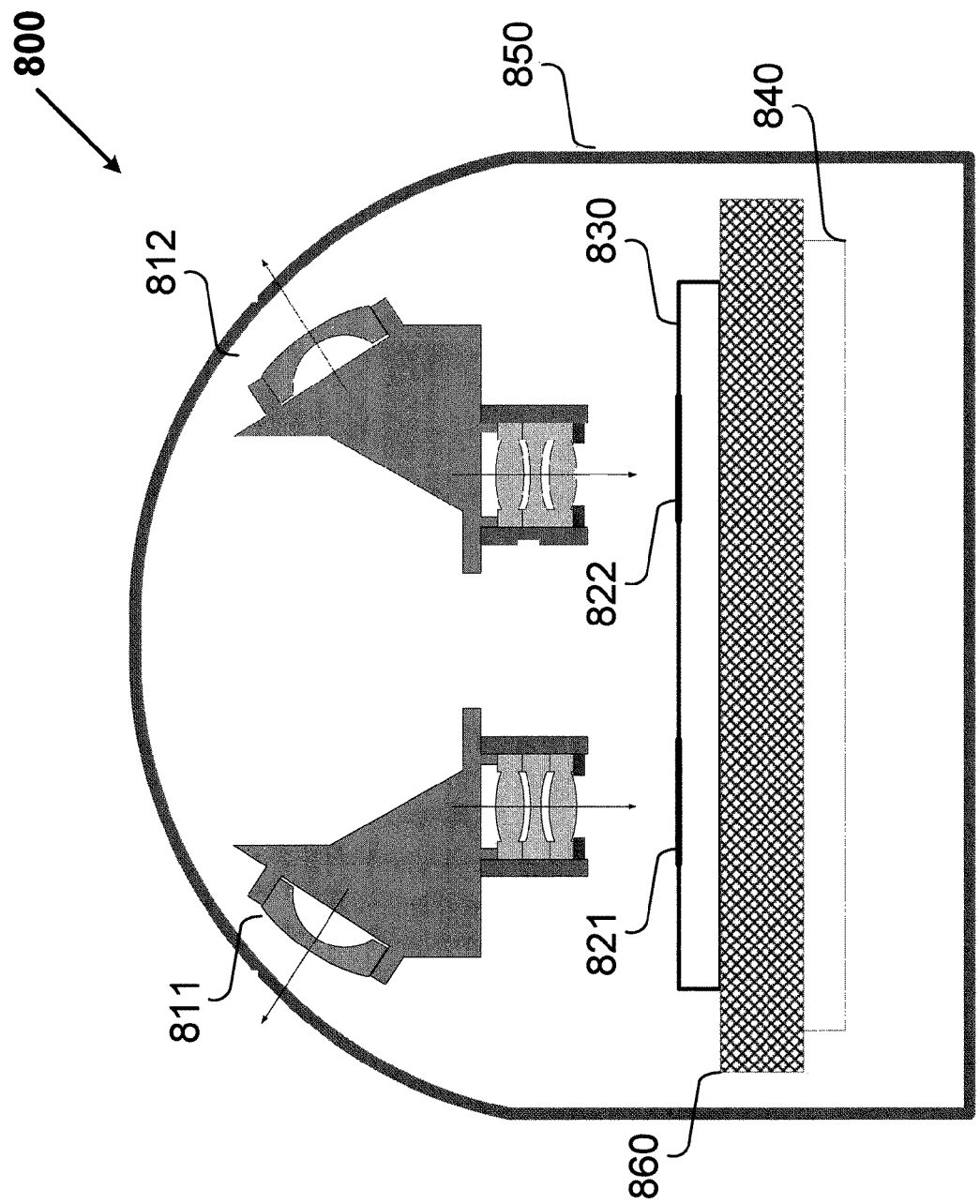
FIG. 8 shows camera system 800 inside a camera housing, in accordance with another embodiment of the present invention.

FIG. 8 shows a cross-section of capsule camera system 800, in accordance with another embodiment of the present invention. Camera system 800 includes an optical system that creates multiple images using multiple lens sub-systems (e.g., lens sub-systems 811 and 812 provide images 821 and 822). In the exemplary embodiment of FIG. 8, a suitable number of suitably positioned lens sub-systems (e.g., four), each consisting of lens elements and prism elements, provide images to image sensor chip 830. Image sensor chip 830 may be provided multiple pixel arrays to captures the images. The output signals from the pixel arrays are combined and digitized on image sensor chip 830 for processing by image processor ASIC 840. Both the image sensor chip 830 and the image processor ASIC 840 can be mounted on PCB 860. Image sensor chip 830 and processor ASIC 840 may be mounted on the same or separate PCBs. Alternatively, image processor ASIC 840 may also be provided outside the camera housing 850, if desired.

Capsule camera system 800 may construct 360° panoramic images from images provided by optical lens sub-systems each having a horizontal field of view of 90° or greater. Such cameras can be used for any applications where wide field of view is desired, such as surveillance cameras and endoscopic cameras.

Thus, the present invention processes multiple images in a less complex, more cost-effective system than prior art imaging systems that use multiple cameras or image sensors. By fabricating multiple pixel arrays on a common sensor chip, the image capturing apparatus may be aligned and supported during manufacturing. Pixel arrays may be formed relative each other with an accuracy of one micron or less. Such a common sensor chip substantially eliminates the additional costs associated with packaging and handling multiple sensor chips beyond the first sensor chip. The reduced complexity results in a lower manufacturing cost. Further, signal processing elements provided on the single chip may be shared among the multiple pixel arrays. Consequently, the silicon area required to implement signal processing functions is reduced, resulting in a smaller die size, lower power, and lower manufacturing cost.

An imaging system of the present invention is also more compact. Under a proper design, a camera system using a single image sensor chip and multiple pixel arrays has a small footprint and can be used wherever a compact design is desired. For example, an imaging system of the present invention may be used in a capsule camera for imaging of the gastro-intestinal (GI) tract. Such an application is described, for example, in U.S. patent application Ser. No. 11/533,304, assigned to Capso Vision, Inc., or in U.S. Pat. No. 5,604,531.

The above detailed description is provided to illustrate specific embodiments of the present invention and is not intended to be limiting. Numerous variations and modifications within the scope of the present invention are possible. The present invention is set forth in the following claims.

We claim:

1. A camera apparatus, comprising:
   a plurality of optical elements forming a plurality of optical paths each forming a separate image from light entering the camera apparatus, wherein the optical elements are configured to provide the separate images on a single image plane and wherein the optical paths each comprise an optical subsystem, each optical subsystem having a field of view greater than a predetermined angle, and wherein the optical systems are positioned to be the predetermined angle apart;

a plurality of sensor arrays fabricated on a common substrate, wherein the sensor arrays are positioned on the single image plane, and wherein each sensor array is positioned to capture a corresponding one of the separate images; and one or more readout circuits coupled to the sensor arrays for reading from the sensor arrays electrical signals representing the separate images captured at the coupled sensor array.

2. The camera apparatus of claim 1, wherein the readout circuits are formed on the common substrate.

3. The camera apparatus of claim 2, wherein the readout circuits are formed at a central location on the common substrate, and wherein the sensor arrays are formed at positions along the periphery of the readout circuits.

4. The camera apparatus of claim 2, wherein a timing and control circuit for controlling the readout circuits and the sensor arrays is formed on the common substrate.

5. The camera apparatus of claim 1, wherein the common substrate comprises a semiconductor substrate.

6. The camera apparatus of claim 5, wherein the sensor array comprises CMOS pixels.

7. The camera apparatus of claim 5, wherein the sensor array comprises CCD pixels.

8. The camera apparatus of claim 1, wherein the fields of view of the optical subsystems cover a horizontal view greater than 180°.

9. The camera apparatus of claim 1, wherein the fields of view of the optical subsystems cover a horizontal view substantially equal to 360°.

10. The camera apparatus of claim 1, further comprising an image processor combining the electrical signals from the sensor arrays to form an image covering the fields of view of the optical subsystems.

11. The camera apparatus of claim 1, wherein predetermined angle is substantially 90°.

12. The camera apparatus of claim 1, further comprising one or more multiplexers provided between the sensor arrays and the readout circuits, such that one or more of the readout circuits are each receiving electrical signals from more than one sensor array.

13. The camera apparatus of claim 1, wherein the electrical signals from each sensor array is provided to a corresponding one of the readout circuits.

14. The camera apparatus of claim 1, further comprising a cover glass provided on a surface of the common substrate.

15. The camera apparatus of claim 1, wherein the optical elements are positioned such that the images are aligned substantially on an image plane.

16. The camera apparatus of claim 1, further comprising a housing in the form of a swallowable capsule for the camera apparatus.

17. The camera apparatus of claim 16, further comprising an image processor receiving the electrical signals of the optical subsystems for constructing an image that combines the images captured by the sensor arrays.

18. The camera apparatus of claim 17, wherein the image processor is provided in an application-specific integrated circuit.

19. The camera apparatus of claim 18, wherein the common substrate and the application-specific integrated circuit are mounted on a printed circuit board.

20. The camera apparatus of claim 16, further comprises a light source and a window through which light from the light source can pass to provide illumination on a subject of which an image is desired.

21. The camera apparatus of claim 16, further comprising a digital storage component for storing data representative of the captured images.

22. The camera apparatus of claim 16, further comprising a display element.

23. The camera apparatus of claim 16, further comprising a transmission element for transmitting data representative of the captured images.

24. The camera apparatus of claim 23, wherein the transmission element supports wireless communication.

25. The camera apparatus of claim 16, further comprises an image compression circuit.

26. The camera apparatus of claim 16, further comprising a power source for powering the camera apparatus.

27. The camera apparatus of claim 1, wherein the electrical signals are digitized.

28. The camera apparatus of claim 1, wherein the optical elements are held together within a lens holder.

29. The camera apparatus of claim 1, wherein the optical elements are enclosed by a lens barrel having a bore for optical elements of each optical path.

30. The camera apparatus of claim 29, further comprises a baffle on top of the lens barrel.

31. The camera apparatus of claim 1, wherein the optical elements are organized into subsystems, each subsystem comprising a negative-power lens element and a positive-power triplet.

32. The camera apparatus of claim 31, wherein the optical elements compensate for chromatic aberration.

33. The camera apparatus of claim 32, wherein the optical elements are organized to provide a folded inverse telephoto lens.

34. A method for providing a panoramic image in a compact camera, comprising:

forming a plurality of optical paths from a plurality of optical elements, each optical path forming a separate image from light entering the camera, wherein the optical elements are configured to provide the separate images on a single image plane;

capturing the images using a plurality of sensor arrays fabricated on a common substrate, wherein the sensor arrays are positioned on the single image plane, and wherein each sensor array is positioned to capture a corresponding one of the separate images;

reading out image data from the sensor arrays representing the separate images captured at the sensor arrays; and processing the image data to provide the panoramic image.

35. The method of claim 34, wherein the image data from the sensor arrays are read out by readout circuits formed on the common substrate.

36. The method of claim 35, wherein the readout circuits are formed at a central location on the common substrate, and wherein the sensor arrays are formed at positions along the periphery of the readout circuits.

37. The method of claim 35, further comprising controlling the readout circuits and the sensor arrays by a timing and control circuit formed on the common substrate.

38. The method of claim 34, wherein the common substrate comprises a semiconductor substrate.

39. The method of claim 38, wherein the sensor array comprises CMOS pixels.

40. The method of claim 38, wherein the sensor array comprises CCD pixels.

41. The method of claim 34, further comprising organizing the optical paths each into an optical subsystem, each optical subsystem having a field of view greater than a predetermined angle, and wherein the optical systems are positioned to be the predetermined angle apart.

42. The method of claim 41, wherein the fields of view of the optical subsystems cover a horizontal view greater than 180°.

43. The method of claim 41, wherein the fields of view of the optical subsystems cover a horizontal view substantially equal to 360°.

44. The method of claim 41, processing the image data comprises combining, in an image processor, image from the sensor arrays to form an image covering the fields of view of the optical subsystems.

45. The method of claim 41, wherein predetermined angle is substantially 90°.

46. The method of claim 34, wherein reading out image data comprises multiplexing a read out circuit to receive image data from more than one sensor array.

47. The method of claim 34, wherein the image data from each sensor array is provided to a corresponding readout circuit.

48. The method of claim 34, further comprising providing a cover glass over a surface of the common substrate.

49. The method of claim 34, further comprising positioning the optical elements such that the images are aligned substantially on an image plane.

50. The method of claim 34, wherein the camera is housed in a swallowable capsule.

51. The method of claim 50, further comprising providing an image processor to receive image data from the optical subsystems for constructing an image that combines the images captured by the sensor arrays.

52. The method of claim 51, wherein the image processor is provided in an application-specific integrated circuit.

53. The method of claim 52, further comprising mounting the common substrate and the application-specific integrated circuit on a printed circuit board.

54. The method of claim 50, further comprises providing a light source and a window through which light from the light source can pass to provide illumination on a subject of which an image is desired.

55. The method of claim 50, further comprising storing data representative of the captured images in a digital storage component.

56. The method of claim 50, further comprising providing a display element inside the housing.

57. The method of claim 50, further comprising transmitting data representative of the captured images to an external receiver.

58. The method of claim 57, wherein the transmission is over wireless communication.

59. The method of claim 50, further comprises compressing the panoramic image in an image compression circuit.

60. The method of claim 50, further comprising powering the camera by an on-board power source.

61. The method of claim 34, wherein the image data are digitized.

62. The method of claim 34, further comprising holding the optical elements together within a lens holder.

63. The method of claim 34, further comprising enclosing the optical elements of each optical path in a bore of a lens barrel.

64. The method of claim 63, further comprises providing a baffle on top of the lens barrel.

65. The method of claim 34, further comprising organizing the optical elements into subsystems, each subsystem comprising a negative-power lens element and a positive-power triplet.

66. The method of claim 65, wherein the optical elements compensate for chromatic aberration.

67. The method of claim 65, wherein the optical elements are organized to provide a folded inverse telephoto lens.

68. An integrated circuit, comprising:
a plurality of sensor arrays fabricated on a common substrate, each sensor array being positioned to capture an image to be projected thereon by a corresponding one of a plurality of optical subsystems each having a field of view greater than a predetermined angle, wherein the optical systems are positioned to be the predetermined angle apart; and
one or more readout circuits formed on the common substrate and coupled to the sensor arrays for reading from the sensor arrays electrical signals representing the images captured at the coupled sensor array, wherein the one or more readout circuits are formed at a central location on the common substrate, and wherein the sensor arrays are formed at positions along the periphery of the one or more readout circuits.

69. The integrated circuit of claim 68, wherein a timing and control circuit for controlling the one or more readout circuits and the sensor arrays is formed on the common substrate.

70. The integrated circuit of claim 68, wherein the common substrate comprises a semiconductor substrate.

71. The integrated circuit of claim 70, wherein the sensor arrays each comprise CMOS pixels.

72. The integrated circuit of claim 70, wherein the sensor arrays each comprise CCD pixels.

73. The integrated circuit of claim 68, further comprising one or more multiplexers provided between the sensor arrays and the one or more readout circuits, such that one or more of the readout circuits are each receiving electrical signals from more than one sensor array.

74. The integrated circuit of claim 68, wherein the electrical signals from each sensor array is provided to a corresponding one of the one or more readout circuits.

75. The integrated circuit of claim 68, further comprising a cover glass provided on a surface of the common substrate.

76. The integrated circuit of claim 68, further comprises an image processing circuit.

77. The integrated circuit of claim 68, further comprises an image compression circuit.

78. The integrated circuit of claim 68, wherein the electrical signals are digitized.

79. An integrated image sensor to be operationally coupled to a plurality of optical components, comprising:
a plurality of pixel arrays formed on a single substrate, each pixel array being positioned for sensing an image in a field of view of a corresponding one of the optical components, wherein the field of view of each optical component is greater than a predetermined angle, and wherein the optical components are positioned to be the predetermined angle apart; and
a processing circuit formed on the single substrate for processing the images sensed by the pixel arrays, wherein a portion of the processing circuit resides between two pixel arrays.

80. The integrated image sensor according to claim 79, wherein the pixel arrays share a common on-chip digital output interface.

81. The integrated image sensor according to claim 79, wherein each optical component has an optical axis and wherein the optical axes of at least two of the optical components are not parallel.

82. The integrated image sensor according to claim 81, wherein the optical axes are disposed at substantially 90° angles.

83. The integrated image sensor according to claim 82, wherein each optical component has a field of view and wherein the fields of field of the optical components overlap so that the composite field of view substantially comprises a 360° panorama.

* * * * *